United States Patent [19]

Diener

[11] Patent Number: 5,683,348
[45] Date of Patent: Nov. 4, 1997

[54] ENDOSCOPE

[75] Inventor: Jörg Diener, Obererdingen, Germany

[73] Assignee: Richard Wolf GmbH, Knittlingen, Germany

[21] Appl. No.: 546,876

[22] Filed: Oct. 23, 1995

[30] Foreign Application Priority Data

Oct. 31, 1994 [DE] Germany ............ 44 38 944.2

[51] Int. Cl.$^6$ ............................................. A61B 1/00
[52] U.S. Cl. .................. 600/143; 600/150; 600/151; 600/139
[58] Field of Search ............................. 600/138, 139, 600/143, 150, 151, 144, 146, 149, 182; 604/281; 138/120, 118, 118.1, DIG. 8

[56] References Cited

U.S. PATENT DOCUMENTS

| | | |
|---|---|---|
| 4,361,139 | 11/1982 | Takagi ............................ 600/182 X |
| 4,601,283 | 7/1986 | Chikama . |
| 4,651,202 | 3/1987 | Arakawa . |
| 4,790,624 | 12/1988 | Van Hoye et al. ............. 600/151 X |
| 4,799,474 | 1/1989 | Ueda ................................. 600/151 |
| 4,919,112 | 4/1990 | Siegmund ..................... 600/146 X |
| 5,482,029 | 1/1996 | Sekiguchi et al. ............. 600/143 X |

FOREIGN PATENT DOCUMENTS

| | | |
|---|---|---|
| A-1019048 | 11/1957 | Germany . |
| A-2912086 | 10/1979 | Germany . |
| A-4222271 | 1/1994 | Germany . |
| 3714492 | 11/1987 | Japan ................................ 600/143 |

*Primary Examiner*—Beverly M. Flanagan
*Attorney, Agent, or Firm*—Panitch Schwarze Jacobs & Nadel, P.C.

[57] ABSTRACT

An endoscope is disclosed which is flexible at least sectionwise and comprises at least one picture guide with an objective arranged at the distal side, and an eyepiece as well as a light guide arranged at the proximal side and a shank surrounding these components. The shank is made from a superelastic material and is dimensioned such that the endoscope is automatically restored to its original shape.

10 Claims, 2 Drawing Sheets

ENDOSCOPE

BACKGROUND OF THE INVENTION

The invention relates to an endoscope which is flexible at least section-wise, having those features specified in the preamble of claim 1.

DESCRIPTION OF THE PRIOR ART

Endoscopes of this type are widely known. Essentially, two types of endoscope are to be distinguished, according to the types of construction: those comprising a hollow shank, in which lumens in the form of tubes are inserted, hereinafter referred to as hollow shank endoscopes; and those which are made from solid material, i.e. those in which the lumens are formed by longitudinal recesses made in the solid material, hereinafter referred to as solid shank endoscopes.

A solid shank endoscope is known for example from DB-A-4222271. A base material, made usually from a plastics material surrounding the individual fibre optics, lumens etc. forms the connection between these. With such endoscopes it is usual, by using an appropriate combination of materials having differing flexibilities and elasticities, to achieve a shank having the characteristics of being pliable, but still being elastically sprung such that it automatically returns to its original position, which is usually an extended position.

Such solid shank endoscopes have advantages as well as disadvantages with regard to their structure as well as their handling, so that in some cases of application, the use of hollow shank endoscopes may be desired. However, hollow shank endoscopes are not generally flexible, and in any case because of the material, may only be guided around large radii of curvature, and in other cases the outer shank must be provided with an additional reinforcement, which prevents unacceptably high tensile stresses from occuring. Such an endoscope is known for example from DB-A-1019948.

DE-A-2912086 discloses the manufacture of a flexible technoscope of a hollow shank construction. This however does not refer to a typical hollow shank instrument since the shank construction is effected by multi-layer steel and plastic compounding. This therefore concerns a reinforced plastic shank. The reinforcement is incorporated into the plastics material thereby ensuring as smooth a peripheral surface as possible. There is further disclosed the provision of a helical spring within the shank, which allows the shank to be automatically returned to its extended position after bending.

Apart from the fact that the shank design is rendered bulky by the sandwich construction, the attachment of an additional helical spring results in a relatively large wall thickness of the shank, which finally leads to the endoscope of such a design having a considerably larger outside diameter than for example, a normal rigid hollow shank technoscope.

SUMMARY OF THE INVENTION

Proceeding from this state of the art, it is the object of this invention to further develop an endoscope of the type previously mentioned, such that with a simple construction, a reduction in its diameter is possible.

In accordance with the invention, this object is achieved with a hollow shank endoscope by forming the outer shank from a superelastic material and dimensioning the shank, such that the endoscope automatically returns to its original shape.

With the solution according to the present invention, the design of a flexible or partly flexible endoscope being compact with regard to the diametrical dimensions is made possible, and from this point of view, makes use of the typical advantages of hollow shank endoscopes, and on the other hand offers those handling advantages of a flexible and automatic return movement endoscope, which are known only in the field of solid shank endoscopes.

The essential advantage of the solution of the present invention is that an indispensable component, namely the outer shank, is not replaced by a spring element for the purpose of return movement as known from the prior art (e.g. DE-A-2912086), but with a suitable choice of materials, is given a further function. It is then clear that in this manner, the diameter of the instrument can be reduced to a minimum.

It is advantageous to construct the instrument such that the shank is not elastic over its whole length but has a rigid distal end. This may be effected in a simple manner by arranging a tube piece, which in any case is required for mounting the objective, at the distal end of the elastic shank. In order to increase the flexibility of the instrument, it is advantageous to place each of the picture and light guides made of a number of glass fibre conductors displacably within the outer shank. With regard to the light guides this does not generally present any problems, since their arrangement with respect to each other is of no significance. However for the picture guides, this is very important since the local distribution over the cross-section of the endoscope at its end, at the objective and eyepiece must correspond to each other. It is useful therefore to set the arrangement of the glass fibres of the picture guide only at the side end, and otherwise not to set the arrangement. In order to make as good use as possible of the available shank cross-section, it is useful to model the light guide such that it fully or at least partly surrounds the picture guide.

It is useful to make the proximal part of the instrument rigid. To this end, at the proximal side, a retaining part is provided, into which the shank runs. An illumination connection is laterally led from this retaining part in a manner already known per se, Here, the picture guide is optically connected to the eyepiece.

In a preferred embodiment the picture guide is arranged concentrically within the shank and the remaining clearance between the picture guide and the shank is taken up by the light guide. Such an embodiment has the advantage that for the same amount of deflection, the bending load on the picture guide always remains the same value, irrespective of the bending direction.

To enable the distal end of the endoscope to be controlled and in particular to be deflected, it is advantageous when at least one control wire is introduced into the shank, fixed to the rigid distal end, its proximal end running into a control mechanism in the retaining part, the control mechanism being known per se. Such control devices are described for example in DE-A-4222271 and DE-A-2912086.

A material particularly suitable for the manufacture of the shank is a nickel-titanium alloy, also known as memory alloy, since this is not only highly flexible but especially permits the design with small wall thicknesses. Finally its resistance to corrosion must be highlighted.

An advantageous outside diameter to wall thickness ratio would be in the range of 9/1 to 15/1, preferably about 12/1.

It is clear that the design according to the invention does not only apply to endoscopes for direct examination with the human eye, but also to so called video endoscopes, with which the observation optics at the distal end, comprising the eyepiece, picture guide and objective, is replaced merely by an electronic picture recording device e.g. a CCD element, the output signal of which being transmitted by an electric cable being fed through the shank, the electric cable being fed into an electric connecting attachment at the recording side.

The design according to the present invention allows for the construction of a partly flexible or flexible endoscope, for example, for examination in the technical field (technoscope), and may achieve a length of e.g. 6 or 10 meters, i.e. lengths which are not possible with conventional endoscopes, due to their lack of rigidity.

BRIEF DESCRIPTION OF THE DRAWINGS

The invention is hereinafter described in more detail by means of embodiments of the invention represented in the drawings. These show.

DETAILED DESCRIPTION OF THE PREFERRED EMBODIMENTS

Figure 3:
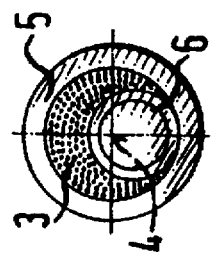
Figure 5:
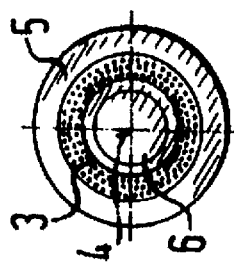

The tube shaped shank 1 formed from superelastic material, in this case a nickel-titanium alloy, encloses a picture guide 2, formed from a multitude of glass fibres, as well as a light guide 3 likewise comprised from a multitude of fibres. The light guide 3, encircles the picture guide 2 almost completely or completely. With the embodiments according to FIGS. 2 and 3 this is effected eccentrically, and with the embodiments according to FIGS. 4 and 5 concentrically with regard to the endoscope axis 4, the light guide filling the space between the shank 1 and the picture guide 2. The fibres of the picture guide 2 and light guide 3 are moveably arranged within the shank 1 in approximately that region where the instrument is made flexible. Only the picture guide is as normal, accordingly fixed within the shank at the end side, thereby allowing a regulated picture transmission. The shank has a diameter to wall thickness ratio of 12/1 and together with the glass fibres situated inside it, is quite flexible, but also has a high resilience, which enables it as much as possible to return to its extended original shape.

Figure 2:
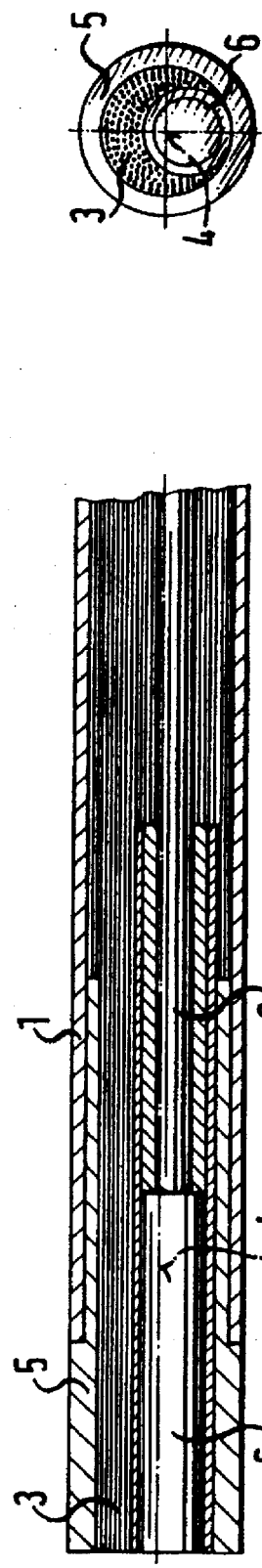
Figure 4:
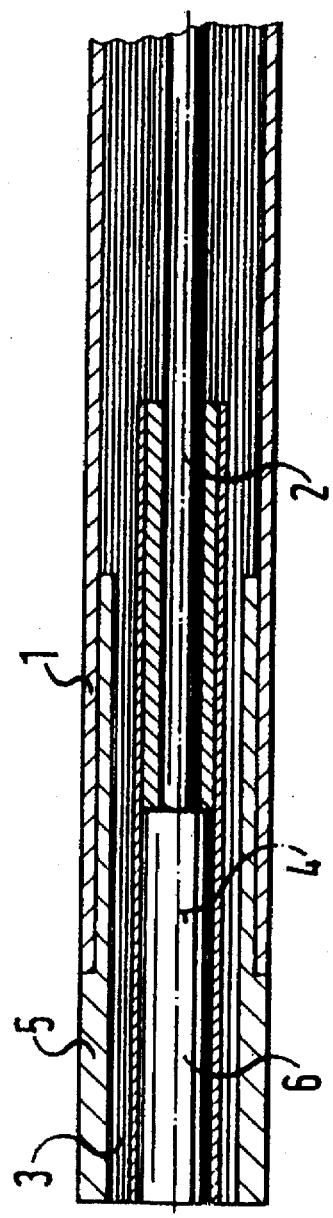

The distal side end of the instrument is formed from an essentially rigid tube piece 5 having the same circumference as the shank 1, as well as a reduced part which is inserted and fixed into the shank 1 (see FIGS. 2 and 4). Within this tube piece 5 is arranged an objective 6 which is optically connected to the distal end of the picture guide 2. The distal ends of the picture guide 2 and light guide 3 are further fixed inside tube piece 5.

Figure 1:
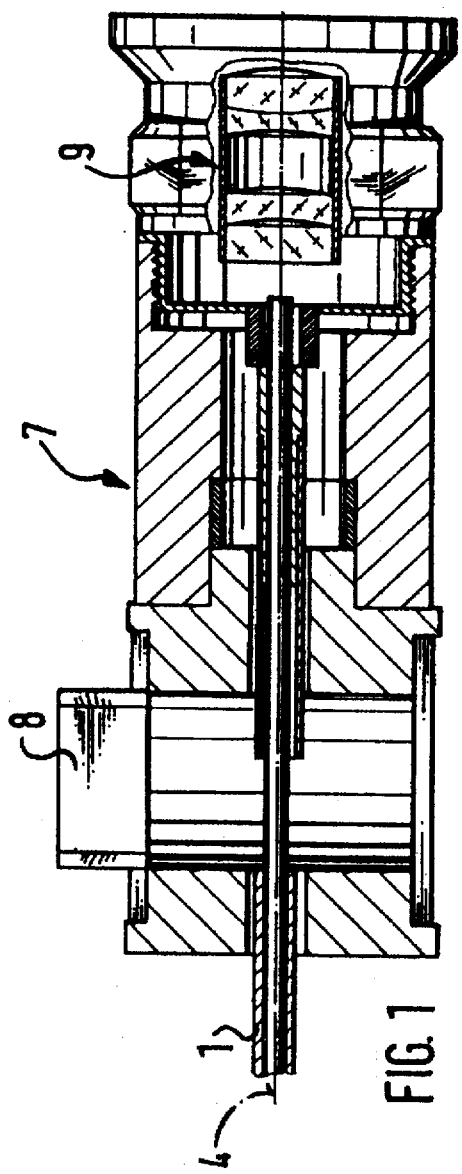
FIG. 1 a diagrammatic representation of a longitudinal cross-section of the proximal side part of the endoscope, FIG. 2 a larger representation of the longitudinal cross-section of the proximal side part of the endoscope, FIG. 3 a view of the distal front end of the endoscope FIG. 4 a concentric embodiment of the endoscope according to the invention represented in FIG. 2, and FIG. 5 one (concentric) embodiment of the endoscope according to the invention represented by FIGS. 2 and 3.

On the proximal side, the shank 1 runs into a rigid retaining part 7, from which the light guide 3 is led out laterally to a light guide connection 8. The proximal end of the retaining part 7 houses the eyepiece optics 9, which are optically connected within the retaining part 7 to the proximal side end of the picture guide. The proximal side part of the picture guide 2 is fixed within a hollow cylindrical component in the retaining part 7, at a distance from the eyepiece optics 9. The retaining part, as shown in FIG. 1, is made from several components, allowing the distance between the eyepiece optics and proximal side end of the picture guide to be changed for the purpose of adjusting the optics.

The above mentioned endoscope is suitable only as an instrument for observation. As a technoscope it permits, in particular, the observation of cavities and cracks as well as long and narrow gaps, which may be concealed by components lying in front of them. The shank 1 requires a restricted guidance at bends so that it can follow them. Generally this does not present any difficulties, and after clearing these bends, the shank returns automatically to its original linear position. Should the clearing of obstacles cause any problems regarding the bending adjustment due to geometric ratios, the instrument may be provided with one or more additional control devices, so that the distal end of the instrument i.e. that rigid part formed by the tube piece 5, may be deflected in a certain direction. The one or more additional control devices include preferably at least one control wire which is introduced into the shank (1) and is fixed in the region of the distal end of the instrument. The proximal end of the control wire is connected to a control mechanism arranged in the retaining part (7).

It can be understood that should it become necessary or advantageous, further inner shanks may be provided inside the shank 1, for example for the introduction of operating instruments, probes or for introducing and carrying off fluids or gases.

I claim:

1. A hollow shank endoscope, flexible at least sectionwise, comprising at least one picture guide (2) with an objective (6) arranged at its distal side, an eyepiece (9) arranged at the proximal side, further comprising at least one light guide (3) and a surrounding tubular shank (1), characterized in that the shank (1) is made from a continuous walled, one-piece, tubular superelastic material and is so dimensioned, that the endoscope is automatically restored to its original shape by mechanical elasticity when the endoscope is removed from a body.

2. An endoscope according to claim 1, characterized in that in the region of the objective (6), the shank is formed by an essentially rigid tube piece (5).

3. An endoscope according to claim 1, characterized in that the picture guide (2) is comprised from a multitude of glass fibres, ordered at least at one end side, and that the light guide (3) is comprised from a multitude of glass fibre conductors, said light guide (3) at least partly surrounding the picture guide (2).

4. An endoscope according to claim 1, characterized in that on the proximal side, the shank (1) runs into a retaining part (7) which laterally incorporates an illumination connection (8) and further incorporates the eyepiece optics (9) on the proximal side to the picture guide.

5. An endoscope according to claim 1, characterized in that the picture guide (2) is arranged concentrically within the shank.

6. An endoscope according to claim 1, characterized in that at least one control wire is introduced into the shank, fixed in the region of the distal end of the instrument, its proximal end connected to a control mechanism arranged in the retaining part (7).

7. An endoscope according to claim 1, characterized in that the shank (1) is made from nickel-titanium alloy.

8. An endoscope according to claim 1, characterized in that the shank (1) has an outer diameter to wall thickness ratio of 9:1 to 15:1.

9. An endoscope according to claim 1, characterized in that instead of the observation optics which comprises the eyepiece, picture guide and objective, there is provided an electronic picture recording arrangement comprising an electronic picture recording device at the distal side and an electrical connection led through the shank to the proximal side.

10. An endoscope according to claim 9, wherein the ratio is about 12:1.

* * * * *